United States Patent [19]

Soldati et al.

[11] 4,219,540
[45] Aug. 26, 1980

[54] METHOD FOR INHIBITING PERSPIRATION

[76] Inventors: Gianluigi Soldati, 486 Flock Rd., Mercerville, N.J. 086109; James W. Stitley, 43 Brooktree Rd., Heightstown, N.J. 08520; Ronald J. Wulf, 207 Varsity Ave.; Herman E. Jass, 77 Poe Rd., both of Princeton, N.J. 08540

[21] Appl. No.: 856,510
[22] Filed: Dec. 1, 1977
[51] Int. Cl.$^2$ .......................... A61K 7/32; A61K 7/38; C07F 5/06
[52] U.S. Cl. .................... 424/65; 260/448 R; 423/263; 423/468; 424/68
[58] Field of Search ............... 424/68, 65; 423/468, 423/263; 260/448 R

[56] References Cited

U.S. PATENT DOCUMENTS

| | | | |
|---|---|---|---|
| 2,794,829 | 6/1957 | Waarden et al. | 260/503 X |
| 3,615,169 | 10/1971 | Thom | 423/263 |
| 3,615,807 | 10/1971 | Yates | 423/263 |
| 3,692,815 | 9/1972 | Thompson | 423/468 |
| 3,796,738 | 3/1974 | Thom | 260/429 R |

OTHER PUBLICATIONS

Chem. Ber., 1970, vol. 103, No. 3, pp. 868–879, Schmeisser et al.
Chem. Abs., 1975, vol. 82, No. 12–13, p. 79777h, Massaux et al.

Primary Examiner—Dale R. Ore
Attorney, Agent, or Firm—Kevin B. Clarke

[57] ABSTRACT

Method of inhibiting perspiration with antiperspirant compositions containing trivalent metal salts of trifluoromethanesulfonic acid of the formula:

$$Me(CF_3SO_3)_3$$

wherein Me is aluminum, lanthanum, cerium or didymium obtained by reacting trifluoromethanesulfonic acid with the appropriate metal carbonate or sulfide or by the exchange reaction of the appropriate metal sulfate with barium trifluoromethanesulfonate.

1 Claim, No Drawings

METHOD FOR INHIBITING PERSPIRATION

BACKGROUND OF THE INVENTION

This invention relates to novel trivalent metal salts suitable for use in various forms of antiperspirant compositions, such as creams, lotions, sticks, pads, powders, aerosols and non-aerosol formulations. This invention further relates to the method of manufacture of such salts and antiperspirant compositions including the novel metal salts of this invention.

Reduction of perspiration flow is dependent upon astringent action in most commercial antiperspirants. The mechanism of this astringency is not well understood. The most popular explanation is that astringents, whose action is limited to the cell surface and the interstitial spaces, by reacting with proteins of the skin cause coagulation and swelling with blocking of the openings of the sweat glands, thus reducing the flow of perspiration. Another explanation is that astringents act directly on the sweat glands, causing inflammation and swelling, thus causing expansion of the stratum corneum around the sweat duct and the orifice, this expansion impeding the sweat flow to the surface. Recent studies have shown, however, that very little active ingredient reaches the dermal layer, which would tend to rule out the theory that the astringents act directly on the sweat glands, and thus limiting the astringency effect to a topical one.

Inorganic salts that have proven to be the most popular in controlling perspiration include the salts of aluminum, zinc, and zirconium. The metal ion of the salt has astringent properties and is responsible for the reaction with the skin tissue to cause coagulation of skin protein. Astringency also appears to be dependent on the anion selected. Among the most commonly employed anions are the chlorides, hydroxychlorides, sulfates and sulfamates.

The most widely used basic aluminum salts are the aluminum chlorohydrates, aluminum chlorohydroxylactates, formed by complexing aluminum chlorohydrate and sodium lactate, basic aluminum bromide, and the aluminum chlorohydrate-propylene glycol and polyethylene glycol complexes. The basic aluminum salts have been used either alone or in admixture with each other and/or complexed with other astringent materials such as aluminum chloride and zirconium hydroxychloride, in antiperspirant preparations.

SUMMARY OF THE INVENTION

This invention relates to efficacious antiperspirant compositions containing as the astringent, compounds of the general formula:

$Me(CF_3SO_3)_3$ wherein Me is aluminum, lanthanum, didymiun or cerium. These compositions are obtained by reacting trifluoromethanesulfonic acid with the appropriate metal carbonate or metal sulfide, or by the exchange reaction of the appropriate metal sulfate with barium trifluoromethanesulfonate; the novel trivalent metal salts of the present invention, including those containing different ratios of metal to acid and complexes thereof, have been found to be effective antiperspirant compositions.

Other lyotropic salts which exhibit anitperspirant action may be used in combination with the compositions of this invention. Such other antiperspirant active compounds include the class of aluminum astringent substances such as aluminum sulfate, aluminum chloride, aluminum chlorohydrate and complexes thereof, the general class of zirconium and titanium astringent compositions such as zirconyl chloride, zirconylhydroxychloride, titanium lactate.

The compositions of this invention are used as stock source of antiperspirant agent from which to prepare with a suitable carrier, any desired antiperspirant composition including powders, creams, lotions, gels and sprays in the form of powders, emulsions, suspensions and solutions. The antiperspirant compositions may be applied by hand or by means of an aerosol, roll-on applicator, squeeze bottle, stick, or a spray-pump. The viscosity and physical form of the antiperspirant composition can be adjusted depending upon the desired mode of application by the usual viscosity controlling agents or thickening agents. It may be desirable, particularly in the case of creams and lotions to employ a suitable emulsifier which is compatible with the carrier and other ingredient. The preferred emulsifier are generally the non-ionic type. Other suitable adjuvant materials to be incorporated into the antiperspirant formulations are emollients, thickeners, opacifying agents, perfume, coloring, buffering and preservative materials.

DETAILED DESCRIPTION OF THE INVENTION

The novel trivalent metal salts of trifluoromethanesulfonic acid which are the subject of the present invention are prepared by reacting, at ambient temperature and pressure, trifluoromethanesulfonic acid with a stirred aqueous slurry of a carbonate or sulfide of aluminum, cerium, lanthanum, or didymium until complete reaction of the acid has occurred. The reaction mixture is then filtered and the filtrate dried at 50°–60° C. under reduced pressure to obtain the desired trivalent metal salt of trifluoromethanesulfonic acid.

Alternatively, the trifluoromethanesulfonic acid salts may be obtained by the exchange reaction attained by combining aqueous solutions of barium trifluoromethanesulfonate with an aqueous solution of aluminum, lanthanum, didymium or cerium sulfate, the mixture filtered and the filtrate dried as above.

The antiperspirant compositions described herein are prepared as described in the following non-limiting examples.

EXAMPLE I

Aluminum Trifluoromethanesulfonate

Trifluoromethanesulfonic acid (100 g.) is slowly added to an aqueous slurry of barium carbonate (65.7 g) of carbonate in 400 ml of water at room temperature and vigorously stirred. At the end of the addition the almost clear solution is filtered twice, then evaporated to dryness at reduced pressure at 60° C. The residue is then dried in an oven at 80° for 24 hours.

43.9 g. of the barium trifluoromethanesulfonate are dissolved in 200 ml of water. To the stirred solution, there are added at room temperature, 22.2 g. of aluminum sulfate dissolved in 150 ml of water. The reaction mixture is then gently heated to 50°–60° C. for 0.5 hours. The warm mixture is then filtered, the filtrate decolorized with charcoal, refiltered and evaporated at reduced pressure and 60° C. to a viscous residue, then dried with a vacuum pump at 50°. The solid residue is collected, grinded and placed in a dessicator over sulfuric acid and under vacuum. The solid analyzed for 4.66% Al and 15.85% S, thus indicating a ratio Al:CF$_3$SO$_3$ of 1:2.87. Yield 25.2 g.

sis of variance tested for statistical probability and experimental error using a computer program.

Data accumulated in the evaluation of these compounds are outlined in the following table.

| Compound | Control Mean | Treated Mean | Percent Reduction | 95% Confidence Limits | Probability |
|---|---|---|---|---|---|
| Cerium Trifluoromethanesulfonate | 0.609 | 0.431 | 29% | 14–42% | 0.0027 |
| Lanthanum Trifluoromethanesulfonate | 0.739 | 0.536 | 27% | 20–34% | 0.0001 |
| Didymium Trifluoromethanesulfonate | 0.688 | 0.436 | 37% | 25–47% | 0.0002 |
| Aluminum Trifluoromethanesulfonate | 0.793 | 0.646 | 19% | 8–28% | 0.0040 |

EXAMPLE II

Cerium Trifluoromethanesulfonate

Trifluoromethane sulfonic acid (45.0 g.) is added dropwise at room temperature to a stirred slurry of 27.5 g. of cerous carbonate in 200 ml of water. After the addition is completed, stirring is continued for 0.5 hours. The slurry is allowed to stand overnight, then is filtered. The filtrate is treated with a small amount of cerium carbonate, stirred and refiltered. The filtrate is then dried at 55°–60° under reduced pressure. The residue is then removed, ground and placed under vacuum in a dessicator, over sulfuric acid. Yield 42.1 g. The solid contains 22.84% Ce; 15.77% S, and 4.50% H$_2$O; Al:S ratio 1:3.01.

EXAMPLE III

Didymium Trifluoromethanesulfonate

Trifluoromethanesulfonic acid is combined dropwise to a stirred slurry of didymium carbonate (15 g.) in 150 ml of water. The reaction mixture is kept at room temperature throughout the addition. The addition of the acid is continued until most of the carbonate is dissolved, and no reaction is observed.

Stirring is continued for 10 minutes, then the reaction mixture is filtered. Didymium carbonate (2 g) is added to ensure complete reaction of the acid. After standing for 5 minutes, the mixture is refiltered and the filtrate dried at reduced pressure at 60° C. The solid residue is stored under vacuum, over sulfuric acid, in dessicator. Yield 22.6 g. The material analysis 27.01% rare earth oxides and 13.51% S.

EXAMPLE IV

Lanthanum Trifluoromethanesulfonate

Lanthanum carbonate (15 g.) and trifluoromethanesulfonic acid (22.5 g) are combined as described in Example II. The solution is evaporated at reduced pressure and the residue, dried over sulfuric acid in dessicator. The product obtained, 20.4 g., gave the following analysis: % La 22.06; % S 15.88; % H$_2$O 5.61, indicating an Al:S ratio of 1:3.12.

The compounds of this invention were tested for antiperspirant activity using an established animal screening model. An experimental design utilized ten test animals in which control and treated sites were compared, with each animal serving as its own control. The products were evaluated as a one percent aqueous solution. Treated sites received exposure to the solution for fifteen minutes and compared to the untreated control site. Percent reductions were calculated as differences between the control and treated areas. An analy- The compositions of this invention can be used in solution or as solids. If a solid material is desired, the solution can be spray-dried, lyophilized or vacuum dried at 50°–60°. Of particular versatility is the aluminum trifluoromethanesulfonate, which is alcohol soluble, and can be utilized in anhydrous pump-sprays.

The following formulations of antiperspirant products, wherein the compositions of this invention are used as the active ingredients, are given as examples only and they are not to be considered limiting or binding.

EXAMPLE V

| ANTIPERSPRIANT ROLL-ON | |
|---|---|
| A) Water, deionized | 50.64 |
| Versene (tetra sodium salt of ethylenediamine tetraacetic acid) | 0.09 |
| Ceraphyl 140 (decyl oleate) | 1.82 |
| Arlacel 165, S. E. (glyceryl monostearate) | 4.54 |
| Veegum HV (aluminum magnesium silicate) | 0.90 |
| B) Cerium Trifluoromethane-sulfonate | 16.36 |
| Water | 25.45 |
| C) Perfume | 0.20 |

EXAMPLE VI

| ANTIPERSPIRANT CREAM | |
|---|---|
| A) Stearic acid | 15.00 |
| Arlacel 60 (sorbitan monostearate) | 5.00 |
| Tween 60 (ethoxylated [20 E. O] sorbitan monostearate) | 5.00 |
| B) Water, deionized | 35.00 |
| C) Lanthanum trifluoromethane-sulfonate | 20.00 |
| Water, deionized | 20.00 |

EXAMPLE VII

| ANTIPERSPIRANT LOTION' | |
|---|---|
| A) Amerchol L101 (lanolin derived sterol extract) | 5.00 |
| Solulan 98 (acetylated poly-oxyethylene lanolin) | 2.00 |
| Cetyl alcohol | 2.00 |
| Myjr 52 (polyethylene glycol 40 stearate) | 4.00 |
| Glycerin | 2.00 |
| B) Veegum HV (aluminum magnesium | |

| ANTIPERSPIRANT LOTION | | |
|---|---|---|
| | silicate) | 1.00 |
| | Water, deionized | 48.00 |
| C) | Didymium trifluoromethane-sulfonate | 18.00 |
| | water | 18.00 |

EXAMPLE VIII

| AEROSOL FORMULATION-PUMP SYSTEM | |
|---|---|
| Isopropyl myristate | 6.0 |
| *Silicone fluid (SF1066) | 2.0 |
| Stearic Acid-triple pressed | 2.0 |
| Alcohol SD40-anhydrous | 80.0 |
| Aluminum Trifluoromethane-sulfonate | 10.0 |

*dimethyl polysiloxane - polyethylene oxide - polypropylene oxide copolymer

The foregoing examples have been illustrative of the invention only and are not to be considered on placing any limitation on the invention. It is recognized that various departures, such as different ratios of metal to acid or complex salts, may be made therefrom within the scope of the accompanying claims without departing from the principles of the invention.

What is claimed is:

1. A method for inhibiting the flow of perspiration from the human body which comprises topically applying to the skin a perspiration inhibiting amount of a compound having the formula:

$$Me(CF_3SO_3)_3$$

wherein Me is selected from the group consisting of aluminum, cerium, didymium or lanthanum.

* * * * *